United States Patent
Iseri et al.

(10) Patent No.: US 11,948,324 B2
(45) Date of Patent: Apr. 2, 2024

(54) ULTRASOUND IMAGING DEVICE, ULTRASOUND IMAGING SYSTEM, ULTRASOUND IMAGING METHOD, AND ULTRASOUND IMAGING PROGRAM

(71) Applicant: FURUNO ELECTRIC CO., LTD., Nishinomiya (JP)

(72) Inventors: Kensuke Iseri, Sakai (JP); Satoshi Nakamura, Takatsuki (JP); Takuo Shimada, Kobe (JP); Tatsuo Arai, Takarazuka (JP)

(73) Assignee: FURUNO ELECTRIC COMPANY LIMITED, Nishinomiya (JP)

( * ) Notice: Subject to any disclaimer, the term of this patent is extended or adjusted under 35 U.S.C. 154(b) by 577 days.

(21) Appl. No.: 17/147,028

(22) Filed: Jan. 12, 2021

(65) Prior Publication Data

US 2021/0174533 A1 Jun. 10, 2021

Related U.S. Application Data

(63) Continuation of application No. PCT/JP2019/024012, filed on Jun. 18, 2019.

(30) Foreign Application Priority Data

Jul. 13, 2018 (JP) ................................. 2018-133146

(51) Int. Cl.
*G06T 7/68* (2017.01)
*A61B 8/00* (2006.01)
(Continued)

(52) U.S. Cl.
CPC ................. *G06T 7/68* (2017.01); *A61B 8/14* (2013.01); *A61B 8/463* (2013.01); *A61B 8/5207* (2013.01);
(Continued)

(58) Field of Classification Search
CPC ......... A61B 8/085; A61B 8/0858; A61B 8/14; A61B 8/463; A61B 8/5207; A61B 8/5253;
(Continued)

(56) References Cited

U.S. PATENT DOCUMENTS

| 5,795,296 A | 8/1998 | Pathak et al. |
| 2010/0179428 A1 | 7/2010 | Pedersen et al. |

(Continued)

FOREIGN PATENT DOCUMENTS

| CN | 103784165 A | 5/2014 |
| CN | 107835663 A | 3/2018 |

(Continued)

OTHER PUBLICATIONS

C. Schulte zu Berge, "Ultrasound Decompression for Large Field-of-View Reconstructions," 2018, Eurographics Workshop on Visual Computing for Biology and Medicine (2018), pp. 1-7.*

(Continued)

*Primary Examiner* — Omar S Ismail
(74) *Attorney, Agent, or Firm* — Studebaker & Brackett PC

(57) ABSTRACT

To provide an ultrasound imaging apparatus capable of displaying an ultrasound stitched image in which an analyte can easily grasp the state of the analyte, an ultrasound imaging apparatus is provided with an ultrasound image generation module which receives ultrasound waves transmitted from a plurality of mutually different positions on the surface of an analyte and reflected in the inside of the analyte and generates ultrasound images corresponding to the respective positions, an image stitcher module which synthesizes the ultrasound images at the respective positions and generates a stitched image of the cross section of the analyte, and a rotation angle adjusting module which adjusts (Continued)

the angle of the stitched image and orients a specific portion included in the stitched image in a predetermined direction.

20 Claims, 16 Drawing Sheets

(51) Int. Cl.
*A61B 8/08* (2006.01)
*A61B 8/14* (2006.01)
*G06T 3/60* (2006.01)

(52) U.S. Cl.
CPC .............. *A61B 8/5253* (2013.01); *G06T 3/60* (2013.01); *G06T 2207/10132* (2013.01); *G06T 2207/20212* (2013.01); *G06T 2207/30004* (2013.01)

(58) Field of Classification Search
CPC ............... A61B 8/5269; A61B 8/5292; G06T 2207/10132; G06T 2207/20212; G06T 2207/30004; G06T 3/60; G06T 7/68
See application file for complete search history.

(56) References Cited

U.S. PATENT DOCUMENTS

| | | | |
|---|---|---|---|
| 2011/0105903 A1* | 5/2011 | Ohnuma | B29C 55/12 600/443 |
| 2013/0078624 A1* | 3/2013 | Holmes | G01N 35/00 73/61.52 |
| 2013/0078733 A1* | 3/2013 | Holmes | B01L 3/50825 422/524 |
| 2013/0079236 A1* | 3/2013 | Holmes | G01N 35/00 204/600 |
| 2013/0079599 A1* | 3/2013 | Holmes | A61B 8/483 600/300 |
| 2013/0109024 A1* | 5/2013 | Rajagopalan | G01N 1/28 435/6.12 |
| 2014/0170735 A1* | 6/2014 | Holmes | G01N 21/76 435/287.1 |
| 2015/0065372 A1* | 3/2015 | Amir | G01N 33/6893 435/6.12 |
| 2016/0077015 A1* | 3/2016 | Holmes | G01N 33/50 506/9 |
| 2016/0320381 A1* | 11/2016 | Holmes | G01N 35/10 |
| 2018/0047555 A1* | 2/2018 | Pringle | H01J 49/26 |
| 2018/0100201 A1* | 4/2018 | Garraway | C21Q 1/6886 |
| 2018/0153509 A1* | 6/2018 | Kremsl | A61B 8/54 |
| 2018/0263596 A1 | 9/2018 | Arai et al. | |

FOREIGN PATENT DOCUMENTS

| | | | | |
|---|---|---|---|---|
| JP | H11-267121 A | 10/1999 | | |
| JP | 2003-038487 A | 2/2003 | | |
| JP | 2006-247039 A | 9/2006 | | |
| JP | 5935344 B2 | 6/2016 | | |
| JP | 2018-068494 A | 5/2018 | | |
| WO | 02/05207 A2 | 1/2002 | | |
| WO | WO-2013043203 A2 * | 3/2013 | ......... | B01L 3/50825 |
| WO | 2017/182278 A1 | 10/2017 | | |
| WO | 2017/186518 A1 | 11/2017 | | |
| WO | 2018079344 A1 | 5/2018 | | |

OTHER PUBLICATIONS

O. Weede, "Knowledge-based Planning of Port Positions for Minimally Invasive Surgery," Mar. 3, 2014, 2013 IEEE Conference on Cybernetics and Intelligent Systems (CIS), pp. 12-16.*

The extended European search report issued by the European Patent Office dated Mar. 7, 2022, which corresponds to European Patent Application No. 19835100.9-1126 and is related to U.S. Appl. No. 17/147,028.

* cited by examiner

ULTRASOUND IMAGING DEVICE, ULTRASOUND IMAGING SYSTEM, ULTRASOUND IMAGING METHOD, AND ULTRASOUND IMAGING PROGRAM

CROSS-REFERENCE TO RELATED APPLICATION(S)

This application is a continuation of PCT International Application No. PCT/JP2019/024012, which was filed on Jun. 18, 2019, and which claims priority to Japanese Patent Application Ser. No. 2018-133146 filed on Jul. 13, 2018, the entire disclosures of each of which are herein incorporated by reference for all purposes.

TECHNICAL FIELD

The present invention relates to an ultrasound imaging apparatus, an ultrasound imaging system, an ultrasound imaging method and an ultrasound imaging program for imaging the inside of an analyte by ultrasound waves.

BACKGROUND

For example, in a medical examination for metabolic syndrome, a CT (Computed Tomography) device or an MRI (Magnetic Resonance Imaging) device is often used to obtain a tomographic image of the abdomen. Since these devices are large and expensive, and there is a problem of exposure to radiation, a technique for obtaining tomographic images using ultrasound waves has been developed in recent years. For example, Japanese Patent No. 5,935,344 discloses a technique of stitching a plurality of ultrasound images obtained by intermittently transmitting ultrasound waves from a probe while moving the probe along the surface of an analyte to generate a stitched image (panoramic image). In this technique, a stitched image showing a cross section of the abdomen can be obtained by simply moving the probe while the analyte makes contact with the abdomen.

For example, in the case of obtaining a tomographic image of the abdomen, the probe is first applied to the vicinity of the flank, and then moved to the vicinity of the opposite flank via the navel. At this time, in the current stitched image, as shown in FIG. 20, the vicinity of the flank corresponding to the initial position of the probe becomes upward. In such a stitched image, since the navel portion does not face upward, there is a problem that it is difficult for the examinee to grasp the state of the abdomen.

SUMMARY

An object of the present invention is to provide an ultrasound imaging apparatus capable of displaying an ultrasound stitched image in which an analyte can easily grasp the state of the analyte.

An ultrasound imaging apparatus according to the present invention is provided with an ultrasound image generation module which receives ultrasound waves transmitted from a plurality of mutually different positions on the surface of an analyte toward the interior of the analyte and reflected therein and generates ultrasound images corresponding to the respective positions, an image stitcher module which synthesizes the ultrasound images at the respective positions and generates a stitched image of the cross section of the analyte, and a rotation angle adjusting module which adjusts the angle of the stitched image and orients a specific portion included in the stitched image in a predetermined direction.

The ultrasound imaging system includes a probe for transmitting ultrasound waves from a plurality of mutually different positions on the surface of an analyte toward the inside of the analyte and receiving the ultrasound waves reflected in the inside of the analyte, and an ultrasound imaging apparatus according to the present invention.

The ultrasound imaging method is characterized by comprising: an ultrasound image generation step of receiving ultrasound waves transmitted from a plurality of mutually different positions on the surface of an analyte toward the inside of the analyte and reflected in the inside of the analyte, and respectively generating ultrasound images corresponding to the respective positions; an image synthesis step of stitching the ultrasound images at the respective positions to generate a stitched image of the cross section of the analyte; and a direction adjustment step of adjusting the angle of the stitched image and directing a specific portion included in the stitched image in a predetermined direction.

An ultrasound imaging program according to the present invention operates a computer as an ultrasound image generation module which receives ultrasound waves transmitted from a plurality of mutually different positions on the surface of an analyte toward the interior of the analyte and reflected therein, and generates ultrasound images corresponding to the respective positions, an image stitcher module which synthesizes the ultrasound images at the respective positions to generate a stitched image of the cross section of the analyte, and a rotation angle adjusting module which adjusts the angle of the stitched image and orients a specific portion included in the stitched image in a predetermined direction.

According to the present invention, it is possible to display an ultrasound stitched image in which an analyte or the like can easily grasp the state of the analyte.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

DETAILED DESCRIPTION

Figure 1:
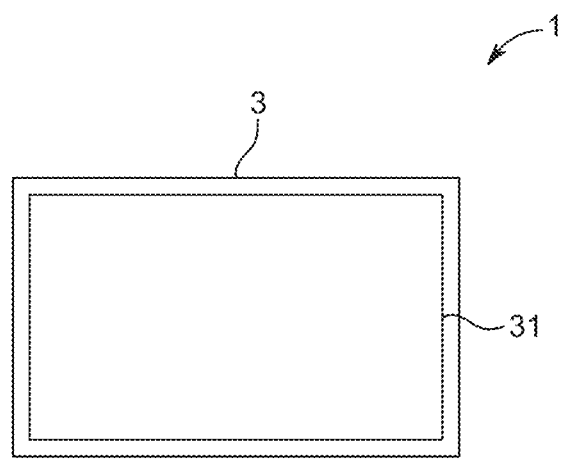
FIG. 1 is a schematic diagram showing a configuration of an ultrasound imaging system according to a first embodiment.
Figure 1:
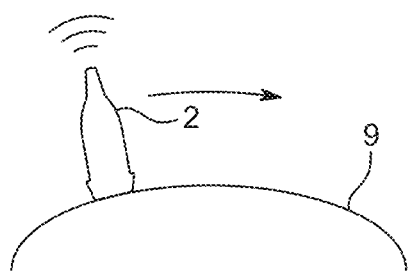

Embodiments of the present invention will now be described in detail with reference to the accompanying drawings. In the following description and the drawings, the same reference numerals indicate the same or similar components, and therefore redundant description of the same or similar components is omitted.

FIG. 1 is a schematic diagram showing a configuration of an ultrasound imaging system 1 according to a first embodiment. The ultrasound imaging system 1 includes a probe 2 and an ultrasound imaging apparatus 3.

The probe 2 is a device for transmitting ultrasound waves from a plurality of mutually different positions on the surface of the analyte 9 toward the inside of the analyte 9 and receiving the ultrasound waves reflected in the inside of the analyte 9, and in this embodiment, the analyte can grasp and move the ultrasound waves. An ultrasound transmission/reception surface in which a plurality of ultrasound vibrators are arranged in a row is provided at the lower end of the probe 2. When obtaining a tomographic image of the analyte 9 (or a cross-sectional image), the analyte makes the ultrasound transmission/reception surface of the probe 2 abut on the analyte 9 and moves the probe 2 along the surface of the analyte 9 (Scan by the probe 2). During this time, the probe 2 intermittently transmits ultrasound waves from the ultrasound transmission/reception surface toward the inside of the analyte 9, and receives the ultrasound waves reflected in the inside of the analyte 9 on the ultrasound transmission/reception surface. Thus, the probe 2 outputs an electric signal (echo signal) indicating the received ultrasound wave.

The probe 2 operates in a linear scan mode for acquiring a linear scan image, but may operate in a sector scan mode for acquiring a sector scan image, may operate in both a linear scan mode and a sector scan mode, or may operate in other modes or in combination with other modes. Further, in the present embodiment, the analyte 9 is mainly the abdomen, but the biological portion included in the analyte 9 is not particularly limited.

The ultrasound imaging apparatus 3 is connected to the probe 2 by radio such as WiFi (registered trademark). In the present embodiment, the ultrasound imaging apparatus 3 is constituted by, for example, a tablet terminal, and has a function of generating a plurality of ultrasound images based on echo signals received from the probe 2, and displaying a stitched image obtained by combining the ultrasound images.

The ultrasound imaging apparatus 3 is not particularly limited as long as it can display an image, and can be configured by a general-purpose personal computer, a smart phone, or the like. The connection method between the probe 2 and the ultrasound imaging apparatus 3 is not particularly limited, and may be a wired connection.

Figure 2:
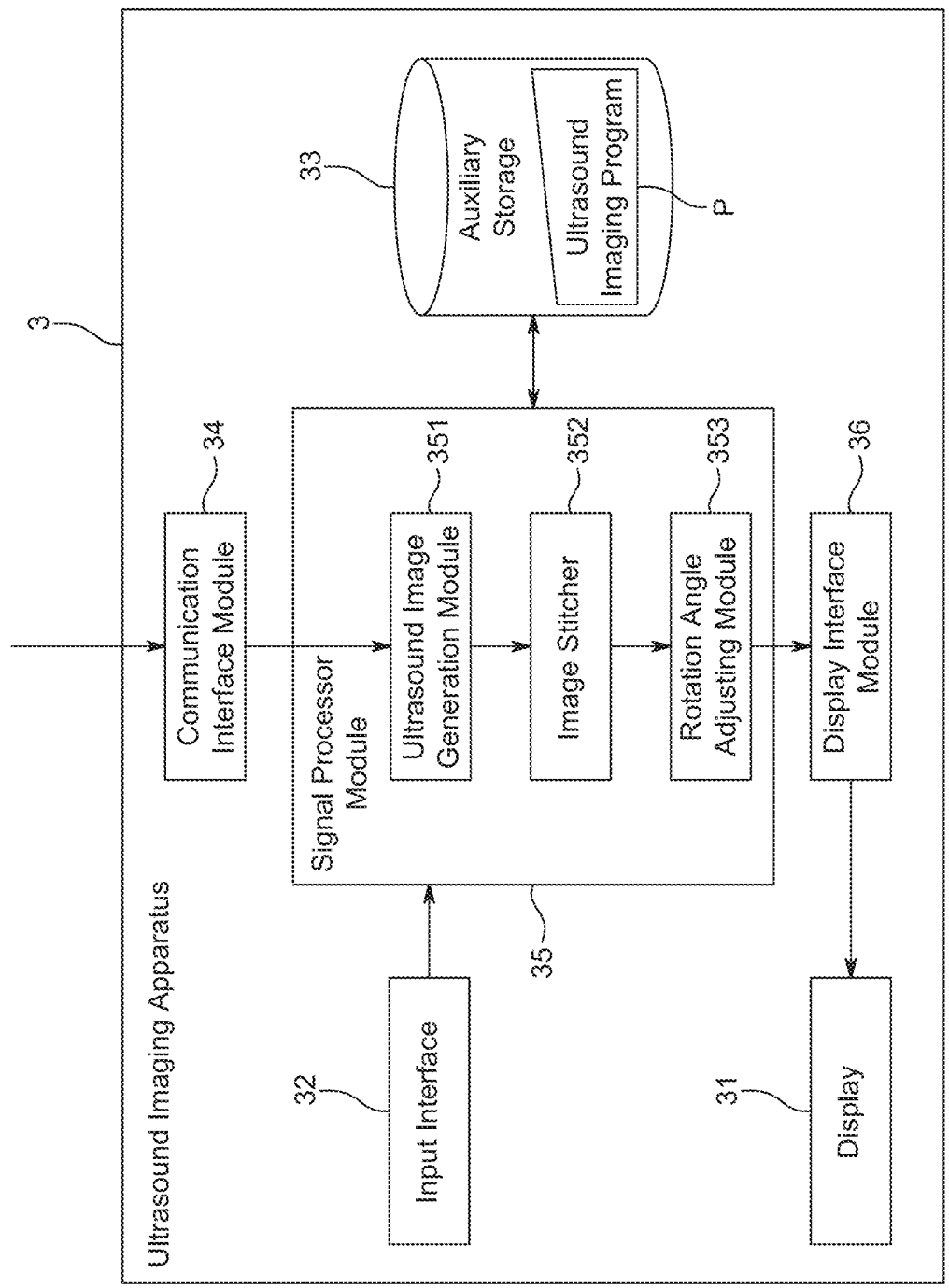
FIG. 2 is a block diagram showing a configuration of an ultrasound imaging apparatus according to a first embodiment.

FIG. 2 is a block diagram showing the configuration of the ultrasound imaging apparatus 3. The ultrasound imaging apparatus 3 includes, as a hardware configuration, a display 31, an input interface 32, an auxiliary storage 33, a communication interface module (I/F module) 34, and a display interface module (I/F module) 36.

The display 31 may be, for example, a liquid crystal display, a plasma display, an organic EL display, or the like. Note that the display 31 may be constructed as a separate device from the ultrasound imaging apparatus 3.

The input interface 32 is a touch panel provided on the surface of the display 31. Through the input interface 32, the analyte can perform an input operation on the image displayed on the display 31.

The auxiliary storage 33 is a non-volatile storage device for storing an operating system (OS), various control programs, and data generated by the programs, and is constituted by, for example, embedded Multi Media Card (eMMC) or Solid State Drive (SSD). The auxiliary storage 33 stores an ultrasound imaging program P. The ultrasound imaging program P may be installed in the ultrasound imaging apparatus 3 via a network such as the Internet. Alternatively, the ultrasound imaging program P may be installed in the ultrasound imaging apparatus 3 by causing the ultrasound imaging apparatus 3 to read a computer-readable non-temporary tangible recording medium such as an SD card on which the ultrasound imaging program P is recorded.

The communication interface module 34 transmits and receives data to and from an external device, and in this embodiment, demodulates a signal received from the probe 2 and modulates a control signal for transmission to the probe 2.

The display interface module 36 displays various image data generated by the arithmetic processing of the ultrasound imaging apparatus 3 on the display 31 by developing the image data in the VRAM, and displays, for example, a stitched image generated by the signal processor module 35 (also referred as "processing circuitry", described later) on the display 31.

Although not shown, the ultrasound imaging apparatus 3 further includes, as other hardware configurations, a processor such as a Central Processing Unit (CPU) for performing data processing, and a memory (main storage) used by the processor in a work area for data processing.

The ultrasound imaging apparatus 3 has a signal processor module 35 as a software configuration. The signal processor module (or "processing circuitry") 35 is a functional block realized by the processor executing the ultrasound imaging program P, and has a function of processing the echo signal received from the probe 2 and displaying the ultrasound stitched image of the analyte 9 on the display 31 so that the analyte, the doctor, the imaging worker, and the like can easily grasp the state of the analyte 9. To realize this function, the signal processor module 35 includes an ultrasound image generation module 351, an image stitcher module 352, and a rotation angle adjusting module 353. The signal processor module (or "processing circuitry") 35 may be implemented in hardware by a logic circuit formed on an integrated circuit.

The ultrasound image generation module 351 generates an ultrasound image inside the analyte 9 from the echo signal received from the probe 2. The probe 2 transmits ultrasound waves toward the inside of the analyte 9 from a plurality of mutually different positions on the surface of the analyte 9 according to a control signal transmitted from the ultrasound imaging apparatus 3 while moving the surface of the analyte 9, receives the ultrasound waves reflected inside the analyte 9, and outputs an echo signal to the ultrasound imaging apparatus 3. Thus, each time the probe 2 receives the ultrasound wave, an echo signal is inputted to the ultrasound image generation module 351, and the ultrasound image generation module 351 generates an ultrasound image corresponding to a plurality of mutually different positions on the surface of the analyte 9 from the echo signal. Although the number of generated ultrasound images varies depending on the transmission/reception time of the ultrasound waves by the probe 2 and the period of transmission/reception, it is assumed that n ultrasound images are generated in this embodiment.

The function of the ultrasound image generation module 351 may be provided in a control device for controlling the probe 2. In this case, the controller may be connected to the ultrasound imaging apparatus 3, or the controller may store the ultrasound image and transmit the ultrasound image to the ultrasound imaging apparatus 3 via a recording medium.

The image stitcher module 352 is a functional block that synthesizes the ultrasound image generated by the ultrasound image generation module 351 at each position on the surface of the analyte 9 to generate a stitched image of the cross section of the analyte 9. Well-known techniques can be applied to the synthesis of ultrasound images, and in this embodiment, for example, the ultrasound images are synthesized using feature point matching between the ultrasound images. In the present embodiment, the term "Section" is a concept including not only a circular cross section but also a partial cross section.

In this method, feature points are detected from the first ultrasound image and the second ultrasound image. Then, the feature points of the first ultrasound image and the second ultrasound image are matched to calculate the homogeneous transformation matrix of the first ultrasound image and the second ultrasound image. Specifically, when the second ultrasound image is rotated clockwise by θ with respect to the first ultrasound image and translated by tx in the x-axis direction and ty in the y-axis direction, and the feature points of the first ultrasound image coincide with those of the second ultrasound image, the homogeneous transformation matrix R for moving the coordinate system of the second ultrasound image to align with the first ultrasound image is:

$$R = \begin{bmatrix} \cos\theta & -\sin\theta & t_x \\ \sin\theta & \cos\theta & t_y \\ 0 & 0 & 1 \end{bmatrix}.$$

That is, when the feature point (x, y) on the 1st ultrasound image moves to the feature point (x', y') on the 2nd ultrasound image, $$\begin{bmatrix} x' \\ y' \\ 1 \end{bmatrix} = R \begin{bmatrix} x \\ y \\ 1 \end{bmatrix}.$$

Since errors are included in the coordinates of the feature points and errors are included in the correspondence relationship itself determined by the influence of noise, outliers adversely affecting calculation are excluded by the Random Sample Consensus (RANSAC) algorithm. A nonlinear least squares method such as the Gauss-Newton method and the Levenberg Marquardt (LM) method can be used for calculating the positional relationship.

The calculation of the homogeneous transformation matrix R is sequentially performed on two ultrasound images in the generation order adjacent to each other up to the n−1 ultrasound image and the nth ultrasound image. Assuming that the homogeneous transformation matrix from the k+1 (1≤k≤n−1) th ultrasound image to the kth ultrasound image is $R_k$, the homogeneous transformation matrix from the k+1 th ultrasound image to the 1st ultrasound image is $R_1 R_2 \ldots R_k$. The coordinate system of the first ultrasound image is called the world coordinate system, and the coordinates of all the ultrasound images can be calculated by calculating a homogeneous transformation matrix to the world coordinate system for all the ultrasound images. Then, the pixels of all the ultrasound images are blended to generate one stitched image.

Figure 20:
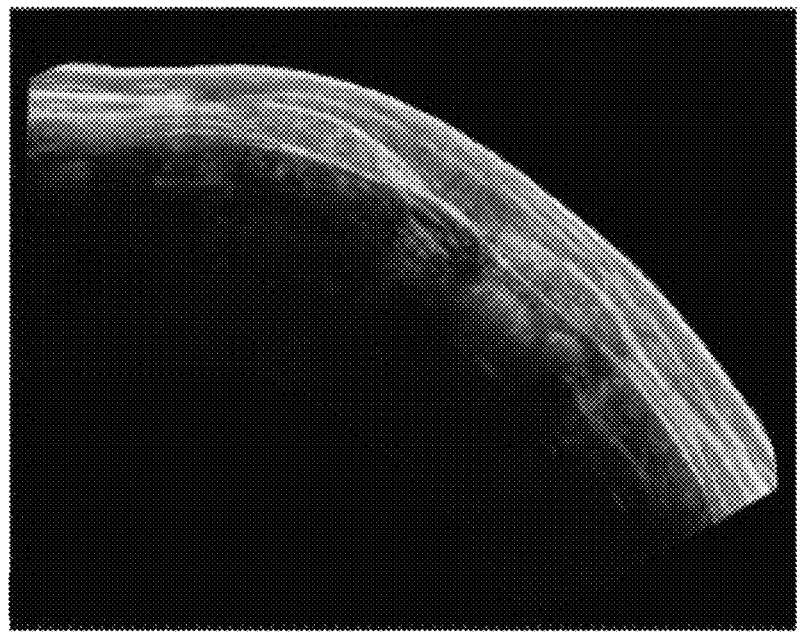
FIG. 20 is an example of a stitched image in which the orientation is not adjusted.

In the present embodiment, it is assumed that a stitched image including the abdominal section shown in FIG. 20 is generated.

The rotation angle adjusting module 353 has a function of adjusting the angle of the stitched image and directing a specific portion included in the stitched image in a predetermined direction. In the present embodiment, the rotation angle adjusting module 353 adjusts the direction of the stitched image shown in FIG. 20 so that the navel portion is in the upward direction, for example. A specific method of adjustment will be described later.

The stitched image whose direction is adjusted by the rotation angle adjusting module 353 is input to the display interface module 36. The display interface module 36 displays the stitched image on the display 31 by developing the data of the stitched image in a Video Random Access Memory (VRAM). It should be noted that the display interface module 36 may display the stitched image on the display 31 once before performing the following direction adjustment, or may display the stitched image on the display 31 after performing the direction adjustment.

Figure 3:
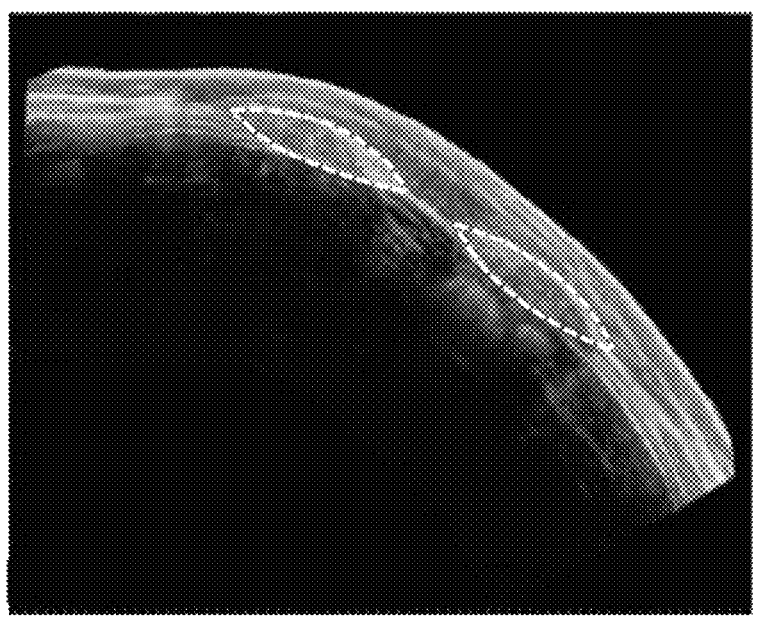
FIG. 3 is an example of a stitched image of an abdominal section.

Hereinafter, an embodiment in which the rotation angle adjusting module 353 adjusts the direction of the stitched image will be specifically described. In the present embodiment, as shown by the broken line in FIG. 3, the direction of the stitched image is adjusted so that the navel portion is upward by utilizing the fact that the cross-sectional shape of the rectus abdominis muscle is generally symmetrical.

Figure 4:
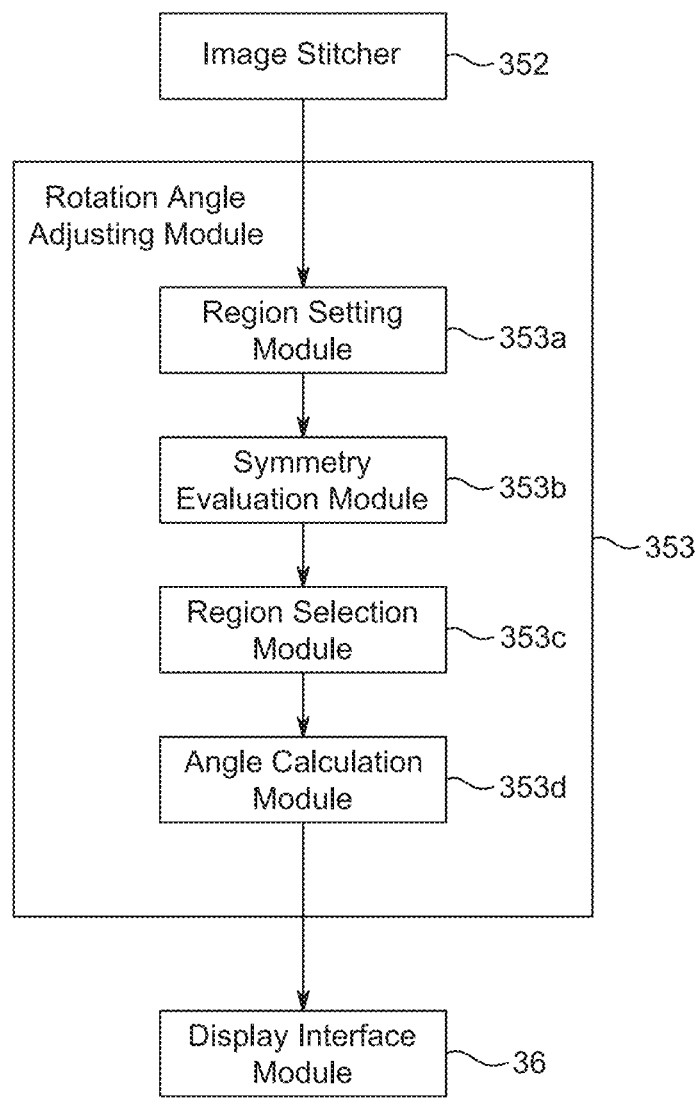
FIG. 4 is a functional block diagram of a rotation angle adjusting module.

As shown in FIG. 4, the rotation angle adjusting module 353 includes a region setting module 353a, symmetry evaluation module 353b, an region selection module 353c, and an angle calculation module 353d.

The region setting module 353a is a functional block for setting one or a plurality of regions r having a shape of line symmetry with respect to the central axis at an arbitrary position and an arbitrary angle. In the present embodiment, the shape of the region r is a rectangle linearly symmetrical with respect to the central axis Ax as shown by the white line frame in FIG. 5. If region r contains the right and left rectus abdominis muscles equally, then the central axis Ax of region r can be considered the central axis through the abdominal umbilicus. The region setting module 353a sets the region r to be movable in order to search for the region r having high left-right symmetry.

Figure 6:
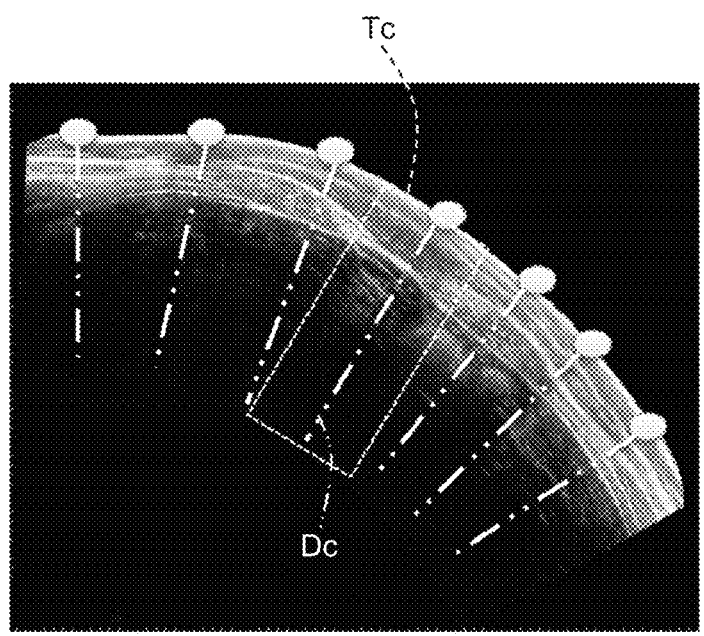
FIG. 6 is an illustration of the probe trajectory and the direction of ultrasound transmission.

More specifically, the region setting module 353a selects one ultrasound image from a plurality of ultrasound images used for generating the stitched image, and sets the region r by aligning the central axis Ax of the region r with an axis indicating the transmission direction of the ultrasound wave at a position on the surface of the analyte 9. That is, the region setting module 353a sets the respective regions r by aligning the central axes Ax of the respective regions r with the respective axes indicating the transmission directions of the ultrasound waves at a plurality of different positions on the surface of the analyte 9. The transmission direction of the ultrasound wave in each ultrasound image can be specified based on the homogeneous transformation matrix of the 1st ultrasound image to the coordinate system (world coordinate system). The locus of the probe 2 at the time of acquiring the ultrasound image corresponds to the upper side of each ultrasound image. Therefore, as shown in FIG. 6, the track of the probe 2 and information on the transmission direction of the ultrasound wave are included in the stitched image.

The region setting module 353a may sequentially select from the 1st ultrasound image to the n-th (n is a positive integer) ultrasound image, but in the present embodiment, the central axis of the central ultrasound image corresponding to the substantially center of the order in which the ultrasound images were generated and the central axes of the central ultrasound images in the order in which a predetermined number of ultrasound images were generated before and after the central ultrasound images are sequentially selected. If n is an even number, the central ultrasound image corresponds to the $\{n/2\}$-th ultrasound image. When n is an odd number, the central ultrasound image corresponds to either the $\{(n-1)/2\}$-th or the $\{(n+1)/2\}$-th ultrasound image. The axis indicating the transmission direction of the ultrasound wave in the central ultrasound image is referred to as Dc. The region setting module 353a first selects a central ultrasound image from the n ultrasound images, and sets the region r by matching the axis Dc of the central ultrasound image with the central axis Ax of the region r indicated by the dashed line in FIG. 5. That is, a region r in which the transmission direction of the ultrasound wave and the central axis of the ultrasound wave in the central ultrasound image coincide is set as a search start region. In the following description, when the transmission direction of the ultrasound wave in the ultrasound image coincides with the central axis of the region, the ultrasound image corresponds to the region.

Thereafter, when the region r is moved, the region setting module 353a selects another ultrasound image, and sets the region r again so that the transmission direction of the ultrasound wave in the selected ultrasound image coincides with the central axis Ax of the region r. In the present embodiment, after selecting the central ultrasound image, the region setting module 353a sequentially selects the ultrasound images (Ultrasound images from $\{(n/2)-(m/2)\}$-th to $\{(n/2)+(m/2)-1\}$-th when m is even) of a predetermined number m before and after the central ultrasound image generation order, thereby moving the region r.

When the analyte 9 acquires an ultrasound image of the abdomen, the probe 2 is normally moved from the vicinity of one side of the abdomen to the vicinity of the other side of the abdomen via the umbilical portion. Therefore, there is a high possibility that the position of the probe 2 at the time of obtaining the central ultrasound image is near the navel portion. Therefore, it is not necessary to search for the regions r having high left-right symmetry in the regions corresponding to all the ultrasound images, and m<n can be set. Thus, the number of times the region r is moved can be suppressed, and the amount of computation can be reduced.

Figure 5:
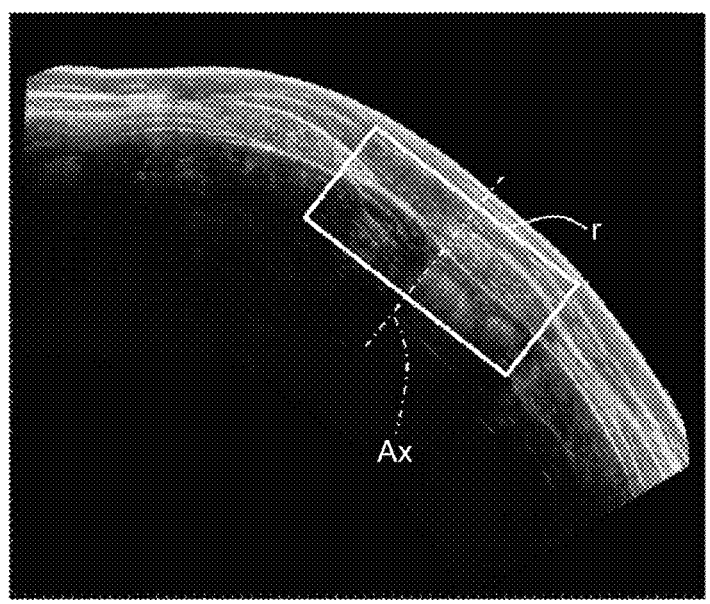
FIG. 5 is an example of a stitched image in which a region is set.

The symmetry evaluation module 353b shown in FIG. 4 is a functional block for evaluating symmetry of each of the left and right images in the region r with respect to the central axis Ax of the region r. For example, when the region r shown in FIG. 5 is set, the symmetry evaluation module 353b evaluates symmetry of the region r by calculating a correlation value between the left region and the right region with respect to the central axis Ax. As the calculation method of the correlation value, for example, Sum of Absolute Difference (SAD), Sum of Squared Difference (SSD), Normalized Cross-Correlation (NCC), and Zero-means Normalized Cross-Correlation (ZNCC) can be used, but ZNCC which is robust against changes in brightness is particularly preferred. For the correlation value, see, for example, http://isl.sist.chukyo-u.ac.jp/Archives/tm.html.

In the stitched image, since the boundary between the muscle such as the rectus abdominis muscle and the other tissue becomes high luminance, a linear pattern is formed. Preferably, the symmetry evaluation module 353b calculates a correlation value of a pattern in the region r.

Instead of the correlation value, symmetry may be evaluated using the mutual information amount. For the amount of mutual information, see, for example, https://lp-tech.net/articles/9 pF3Z.

Figure 7:
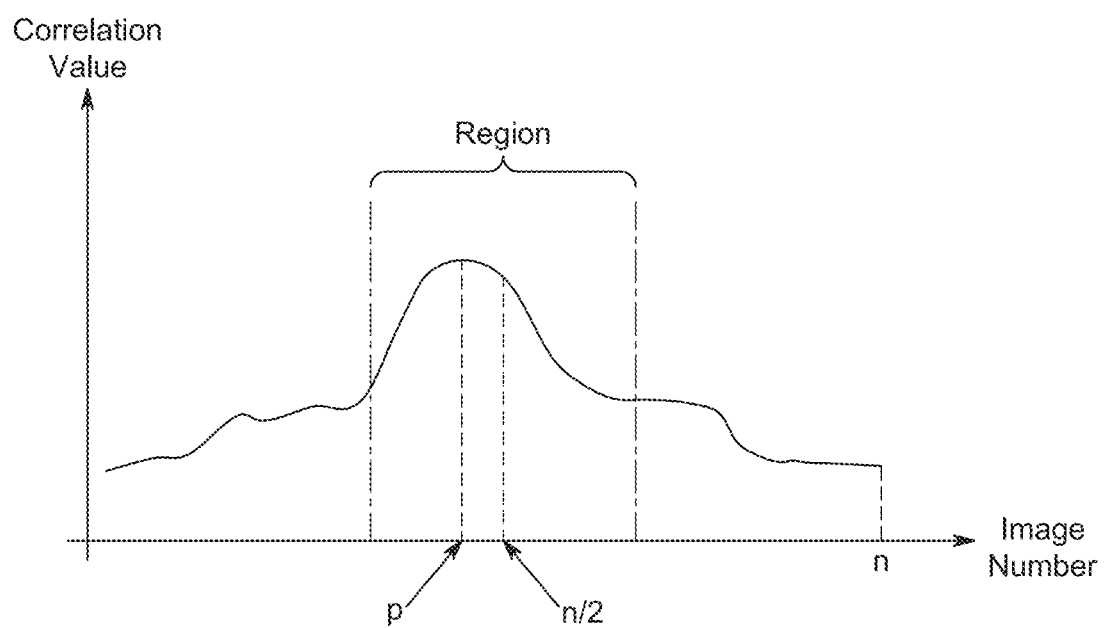
FIG. 7 is a graph showing an example of the relationship between the number of ultrasound images corresponding to a region and a correlation value.

The symmetry evaluation module 353b evaluates each symmetry of all the regions r set by the region setting module 353a, and records each symmetry in the memory each time the regions r move. FIG. 7 is a graph showing an example of the relationship between the Image number of the ultrasound image corresponding to the region and the correlation value.

Figure 8:
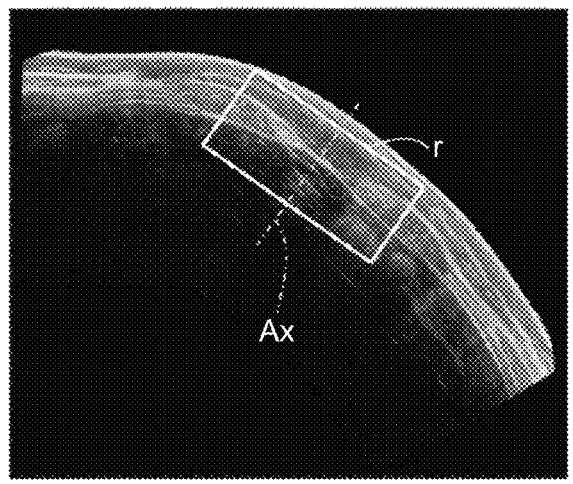
FIG. 8 is an example of a stitched image in which a region is set approximately in the middle of the rectus abdominis muscle.

The region selection module 353c is a functional block for selecting a region r based on symmetry. In the present embodiment, the region selection module 353c selects the region r (In the example shown in FIG. 7, a region corresponding to the p-th ultrasound image is shown.) having highest symmetry from the regions r whose symmetry have been evaluated. Thus, as shown in FIG. 8, the region r in which the central axis Ax is located substantially in the middle of the right and left rectus abdominis muscles is selected.

The region selected by the region selection module 353c need not necessarily be a region having the highest symmetry, but may be any region having symmetry equal to or greater than a predetermined threshold value. For example, a region having a relatively high symmetry such as the second highest symmetry may be selected.

Figure 9:
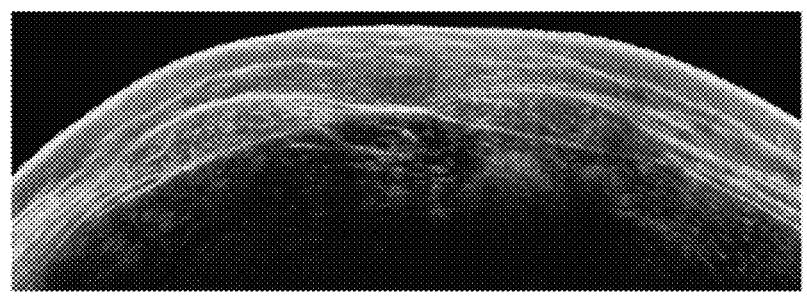
FIG. 9 is an example of an orientation-adjusted stitched image.

The angle calculation module 353d is a functional block for calculating an angle difference between a predetermined axis passing through the stitched image and the central axis Ax of the selected region r, and the rotation angle adjusting module 353 adjusts the angle of the stitched image based on the angle difference calculated by the angle calculation module 353d. In the present embodiment, the predetermined axis passing through the stitched image is the left-right symmetry axis of the stitched image. Thus, the stitched image is rotated so that the central axis Ax shown in FIG. 8 is directed upward. The data of the stitched image adjusted by the rotation angle adjusting module 353 is output to the display interface module 36, and the stitched image with the navel portion facing upward as shown in FIG. 9 is displayed on the display 31. Thus, the analyte 9 can easily grasp the state of the abdomen. Although, only a part of the stitched image is displayed in FIG. 9, it goes without saying that the entire stitched image may be displayed.

The shape of the region r is not particularly limited as long as it is symmetric with respect to the central axis, and may be, for example, an isosceles trapezoid, a rhombic, a hexagonal, an elliptical, or the like. Further, although the size of the region r is not particularly limited, it is preferable that the width of the region r be different from the width of each of the rectus abdominis muscles because each of the right and left rectus abdominis muscles has a substantially symmetrical shape.

When the analyte 9 makes the probe 2 abut on the analyte 9, the transmission direction of the ultrasound wave is not necessarily perpendicular to the surface of the analyte 9. In particular, if the transmission direction of the ultrasound wave is not perpendicular to the surface of the analyte 9, when the probe 2 passes near the navel portion, there is a possibility that the region set near the navel portion is inclined with respect to the direction in which the rectus abdominis muscles are connected and symmetry is not increased.

Figure 10:
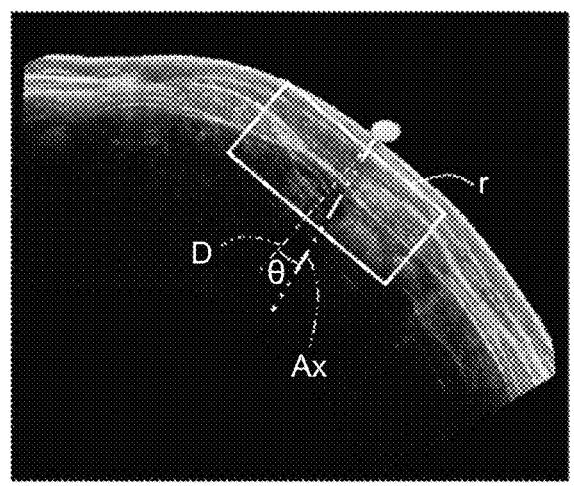
FIG. 10 is a diagram illustrating another example of setting of the region.

Therefore, the region setting module 353a may set the area r such that the angle θ between the axis D indicating the transmission direction of the ultrasound wave in the selected ultrasound image and the central axis Ax of the area r is not more than a predetermined value, as shown in FIG. 10. The predetermined value is not particularly limited, but is set to an assumed maximum value (for example +/−5°) of the angle formed by the transmission direction of the ultrasound wave and the normal of the surface of the analyte 9 in the normal movement of the probe 2. In this case, the region setting module 353a selects one ultrasound image, sets the region r, and then changes the angle θ by, for example, 1° to move the region r. Each time the angle θ changes, the symmetry evaluation module 353b evaluates the symmetry of the region r, and the region selection module 353c selects the region r having the highest symmetry. Thus, even if the transmission direction of the ultrasound wave is not perpendicular to the surface of the analyte 9, the area r set near the navel portion has the highest symmetry at any angle, so that an appropriate area can be selected.

Figure 11:
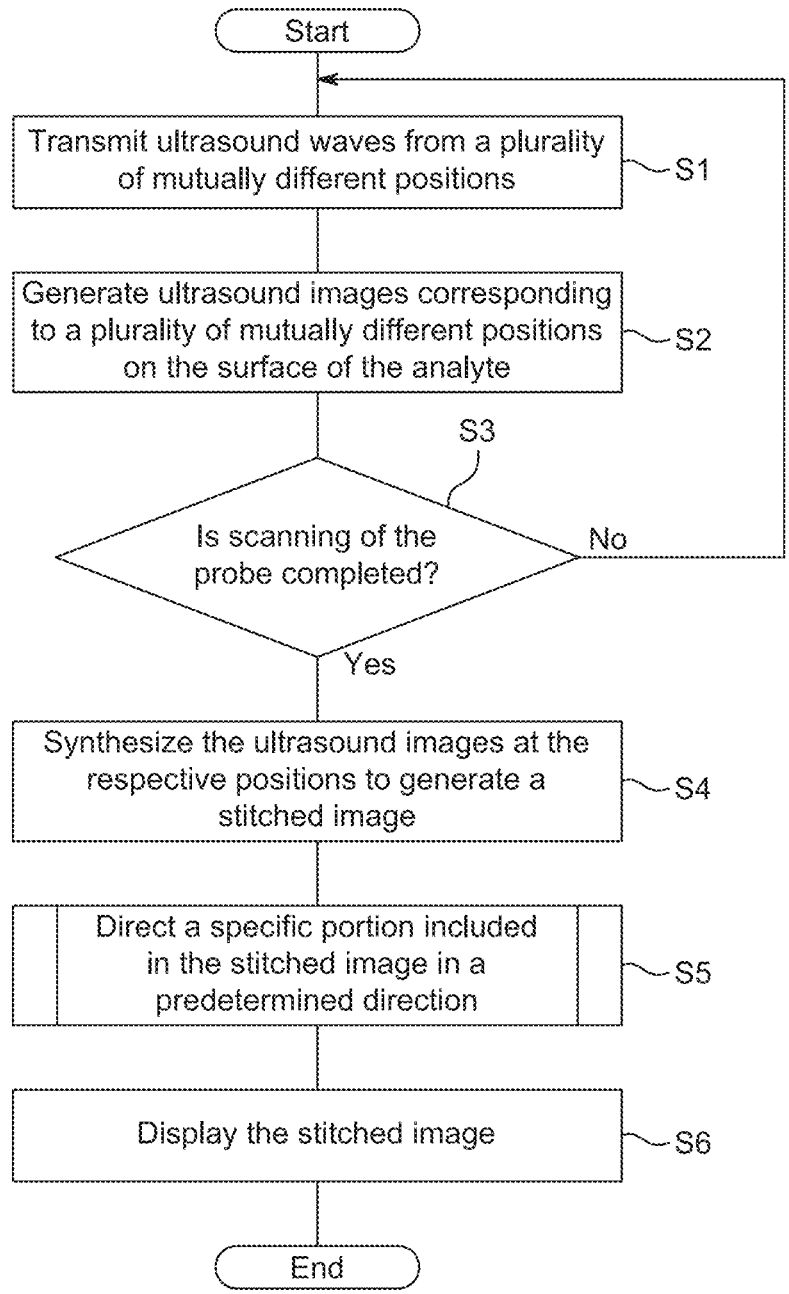
FIG. 11 is a flowchart showing a processing procedure of the ultrasound imaging method according to the first embodiment.

FIG. 11 is a flowchart showing the processing procedure of the ultrasound imaging method according to the present embodiment.

In step S1, the probe 2 transmits ultrasound waves from a plurality of mutually different positions on the surface of the analyte 9 toward the inside of the analyte 9. Thus, the probe 2 receives the ultrasound wave reflected inside the analyte 9 and outputs an echo signal from the probe 2.

In step S2, the ultrasound image generation module 351 generates ultrasound images corresponding to a plurality of mutually different positions on the surface of the analyte 9. In this embodiment, each time an echo signal is output from the probe 2, the ultrasound image generation module 351 generates an ultrasound image. In step S3, it is checked if the scanning of the probe 2 is completed. Steps S1 and S2 are repeated until the scanning of the probe 2 is completed.

When the scanning of the probe 2 is completed, in step S4 (image synthesis step), the image stitcher module 352 synthesizes the ultrasound images at the respective positions to generate a stitched image of the cross section of the analyte 9.

Subsequently, in step S5 (orientation step), the rotation angle adjusting module 353 directs a specific portion included in the stitched image in a predetermined direction. The adjustment by the rotation angle adjusting module 353 may be performed automatically after generation of the stitched image, or may be performed when a predetermined operation via the input interface 32 or the like is received. A more detailed processing procedure of step S5 will be described later.

Thereafter, in step S6 (display step), the stitched image whose orientation is adjusted is displayed on the display 31.

Figure 12:
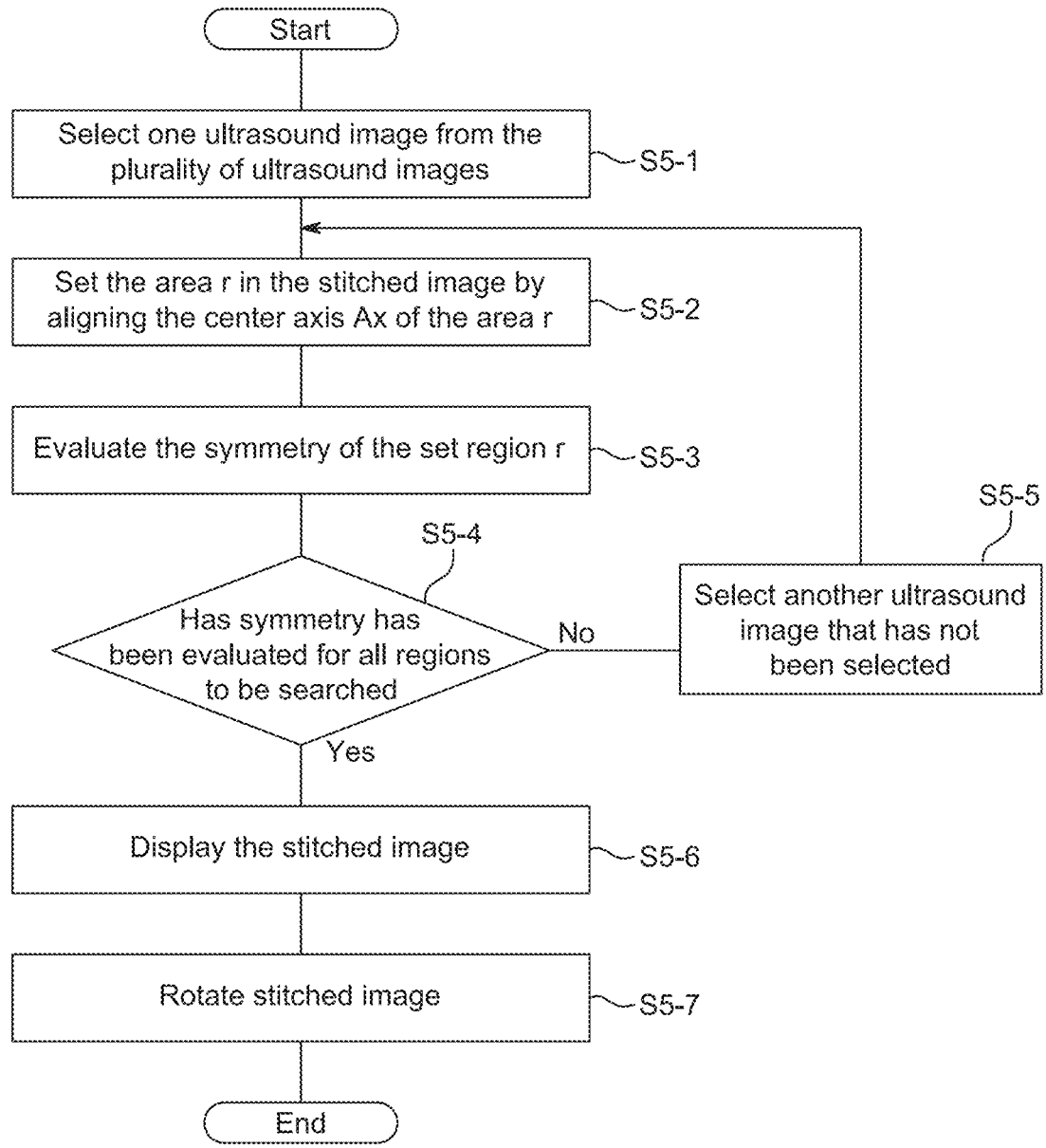
FIG. 12 is a flowchart showing a detailed processing procedure of the direction adjusting step in the first embodiment.

FIG. 12 is a flowchart showing a detailed processing procedure of step S5 in this embodiment. Step S5 includes steps S5-1 to S5-7.

First, in step S5-1, the region setting module 353a selects one ultrasound image from the plurality of ultrasound images used for generating the stitched image. In this embodiment, for example, a central ultrasound image corresponding to the center of the order of generation of the ultrasound image is selected.

Subsequently, in step S5-2, the region setting module 353a sets the area r in the stitched image by aligning the central axis Ax of the area r with an axis indicating the transmission direction of the ultrasound wave in the selected ultrasound image.

Subsequently, in step S5-3, the symmetry evaluation module 353b evaluates the symmetry of the set region r. In step S5-4, it is checked if symmetry has been evaluated for all regions to be searched.

If symmetry has not been evaluated for all regions to be searched, the process proceeds to step S5-5, in which the region setting module 353a selects another ultrasound image that has not been selected. Then, steps S5-2 and S5-3 are performed for the other selected ultrasound images. Steps S5-2, S5-3, and S5-5 are repeated until symmetry is evaluated for all regions to be searched.

Thereafter, in step S5-6, the region selection module 353c selects, for example, the region r having highest symmetry. It should be noted that the region selection module 353c may select a region r having a relatively high symmetry, such as a region having a second highest left-right symmetry.

Subsequently, in step S5-7, the angle calculation module 353d calculates an angle difference between the left-right symmetric axis of the stitched image and the central axis Ax of the region r selected by the region selection module 353c, and the rotation angle adjusting module 353 rotates the stitched image by adjusting the angle of the stitched image based on the angle difference.

As described above, in the present embodiment, using the fact that the cross-sectional shape of the rectus abdominis muscle is generally symmetrical, the orientation of the stitched image is adjusted so that the navel portion is upward. Thus, a stitched image in which the state of the abdomen is easily grasped can be displayed on the analyte 9 or the like.

It should be noted that the technique of the present embodiment can be applied to a portion other than the rectus abdominis muscle as long as the portion includes a generally symmetrical tissue. Such areas include the back, waist, and neck.

Figure 13:
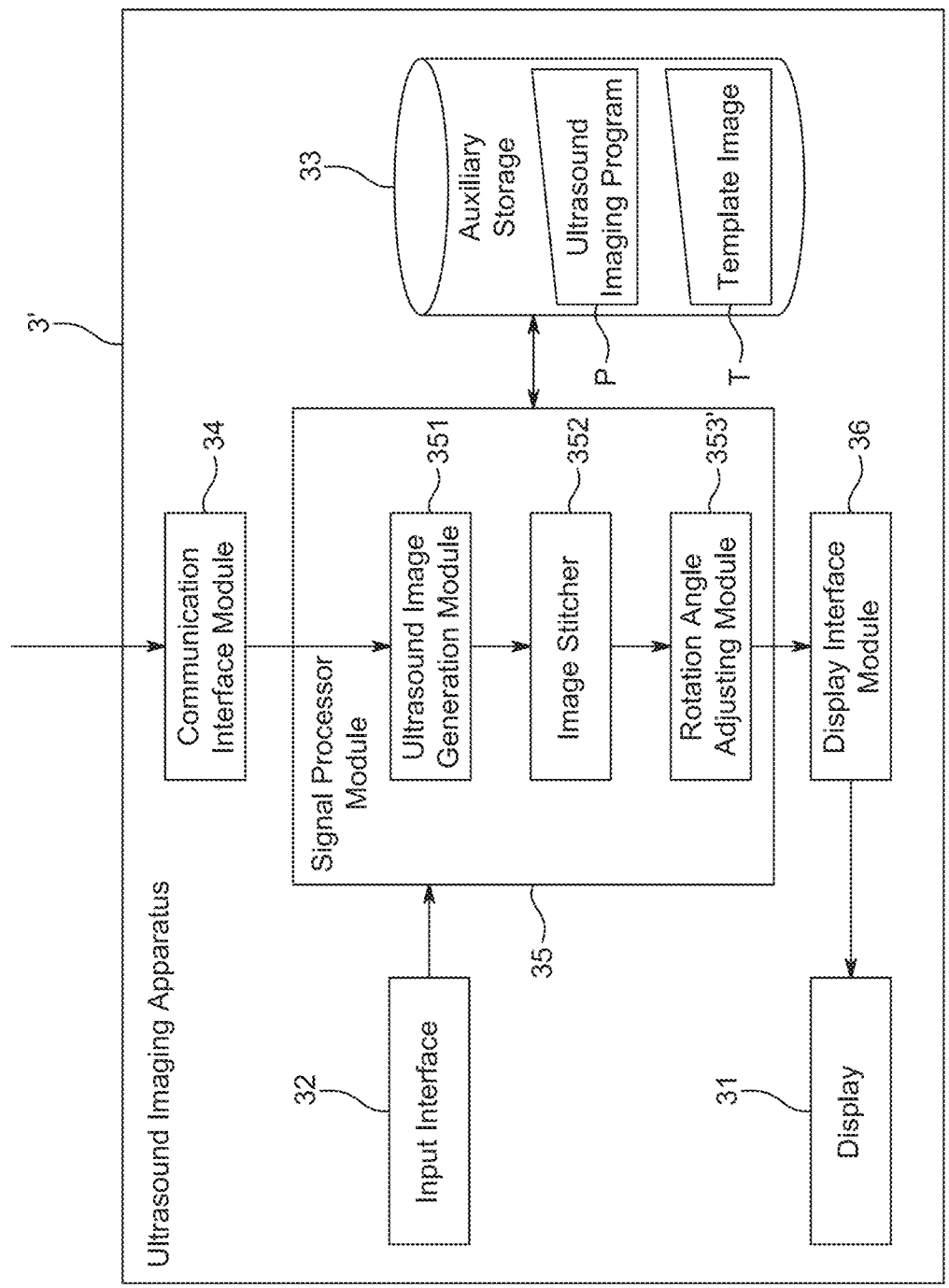
FIG. 13 is a block diagram showing a configuration of an ultrasound imaging apparatus according to a second embodiment.

In the second embodiment, the orientation of the stitched image is adjusted by comparing the stitched image with the template image while rotating the stitched image. FIG. 13 is a block diagram showing the configuration of the ultrasound imaging apparatus 3' according to the second embodiment. In the ultrasound imaging apparatus 3' shown in FIG. 2, the rotation angle adjusting module 353 is replaced with the rotation angle adjusting module 353'. A template image T is stored in the auxiliary storage 33.

Figure 14:
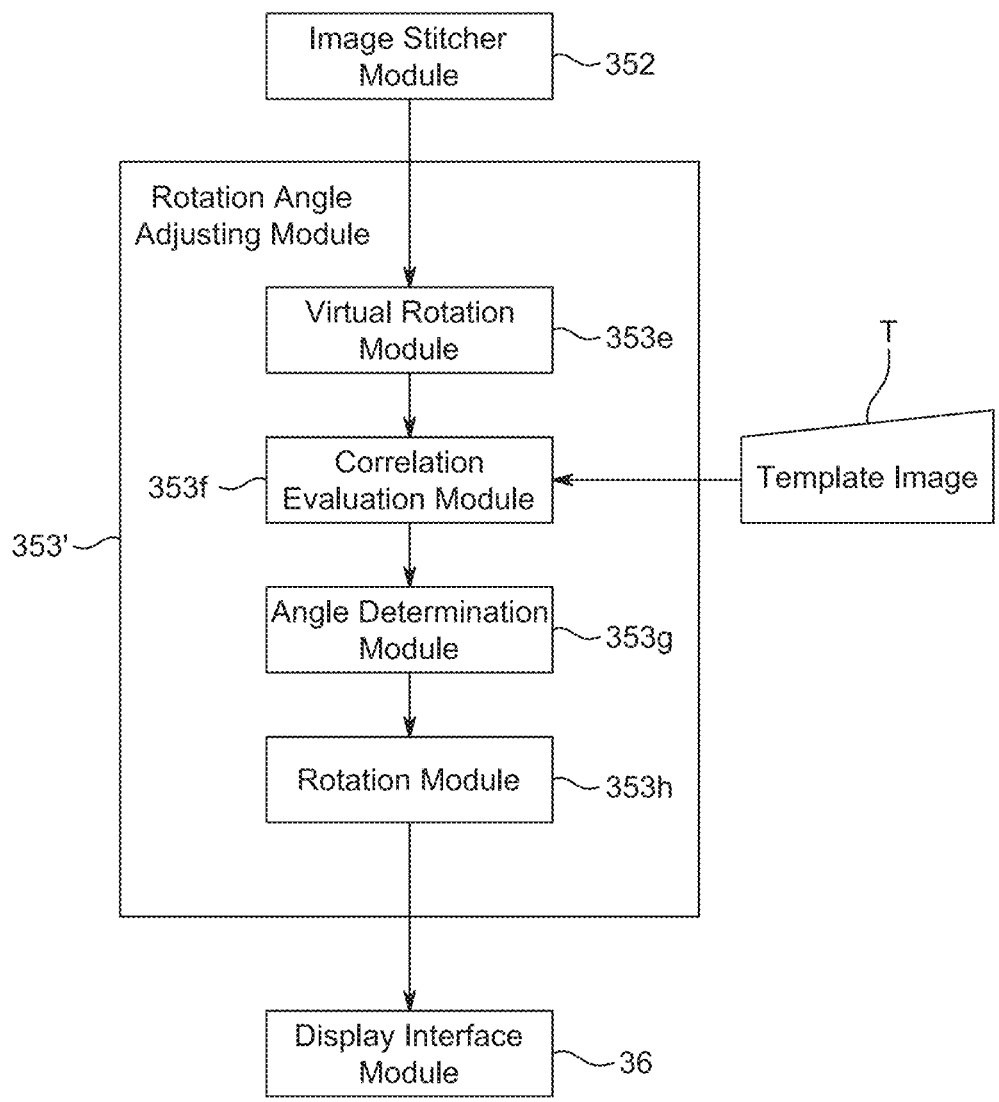
FIG. 14 is a functional block diagram of a rotation angle adjusting module in a second embodiment.

FIG. 14 is a block diagram showing functions and the like of the rotation angle adjusting module 353'. . . . The rotation angle adjusting module 353' includes a virtual rotation module 353e, a correlation evaluation module 353f, an angle determination module 353g, and a rotation module 353h.

Figure 15:
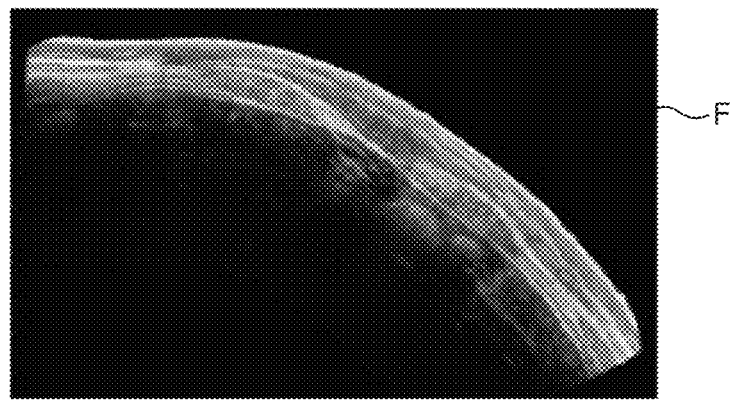
FIG. 15 shows an example of a stitched image to be adjusted.

The virtual rotation module 353e is a functional block that virtually rotates at least one of the template image T of the ultrasound stitched image and the stitched image generated by the image stitcher module 352. The template image T in the present embodiment includes a navel portion (specific site) and is an ultrasound stitched image showing a cross section of an abdomen in which the navel portion is directed upward (predetermined direction). The template image T can be created by averaging abdominal ultrasound stitched images of a plurality of individuals. Alternatively, if an ultrasound stitched image of the same analyte has been generated in the past, the stitched image of the past analyte whose direction is adjusted may be used as the template image T. In this embodiment, it is assumed that the stitched image whose direction is adjusted is the template image T, and the stitched image F shown in FIG. 15 is newly generated.

Although the virtual rotation module 353e may rotate the template image T, in this embodiment, only the stitched image F is rotated. The virtual rotation module 353e may rotate the stitched image F by 360°, but in the present embodiment, based on the fact that the outer shape of the cross section of the template image T is substantially an arc shape directed upward, and the outer shape of the cross section of the stitched image F is substantially an arc shape inclined rightward, the stitched image F is rotated counter clockwise within a range of, for example, 45°. The outer shape of the cross section of the stitched image F can be determined, for example, from the coordinates of the left end portion corresponding to the contact position of the probe 2 at the start of scanning, the right end portion corresponding to the contact position at the end of scanning, and the respective portions of the central portion corresponding to the contact position at the time point in the middle between the start and end of scanning.

Figure 16:
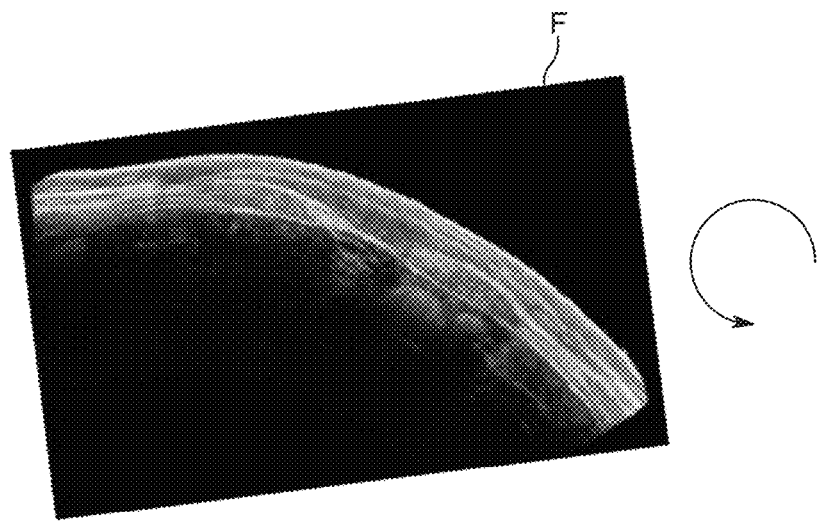
FIG. 16 is an example of a rotated stitched image.

The angle at which the virtual rotation module 353e rotates the stitched image F at one time is not particularly limited, but in this embodiment, the stitched image F is rotated by 1<at a predetermined angle, for example. An example of the rotated stitched image F is shown in FIG. 16.

Figure 17:
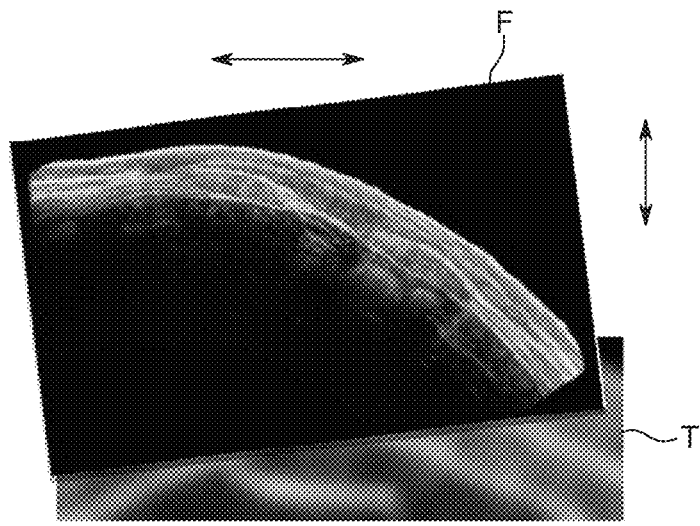
FIG. 17 is a diagram illustrating matching between a stitched image and a template image.

The correlation evaluation module 353f is a function block for evaluating the correlation between the template image T and the stitched image. Specifically, each time the virtual rotation module 353e rotates the stitched image F, the correlation evaluation module 353f matches the stitched image F with the template image T while virtually moving the rotated stitched image F as shown in FIG. 17, and specifies the relative position at which the correlation value between the stitched image F and the template image T becomes maximum. The correlation evaluation module 353f records the correlation value at the specified relative position in the memory as the correlation for each rotation angle from the initial position of the stitched image F.

The calculation method of the correlation value may be the same as that of the first embodiment, and the mutual information amount may be used instead of the correlation value. The rotation of the stitched image F by the virtual rotation module 353e and the matching between the stitched image F and the template image T by the correlation evaluation module 353f are virtual and need not be displayed on the display 31. When the virtual rotation module 353e rotates the stitched image F one time, the correlation evaluation module 353f may terminate the correlation evaluation process if the correlation is equal to or greater than a predetermined threshold value.

The angle determination module 353g shown in FIG. 14 is a functional block for determining the rotation angle of the stitched image F based on the correlation evaluated by the correlation evaluation module 353f. The rotation angle here means an angle at which the stitched image F is actually rotated by the rotation module 353h described later. In the present embodiment, the stitched image Fmax having the highest correlation is selected from the stitched images F evaluated with the correlation, and the angle with respect to the initial position of the stitched image Fmax is determined as the rotation angle of the stitched image F.

The stitched image selected by the correlation evaluation module 353f is not necessarily the stitched image having the highest correlation, and may be any stitched image having a correlation value equal to or higher than a predetermined threshold value. For example, a stitched image having a relatively high correlation, such as a stitched image having the second highest correlation, may be selected.

The rotation module 353h is a functional block for rotating the stitched image F according to the rotation angle determined by the angle determination module 353g. Since the stitched image F rotated by the rotation module 353h is a stitched image evaluated to have the highest correlation with the template image T, the navel portion is adjusted to be substantially upward. The rotation module 353h outputs the data of the rotated combined image to the display interface module 36, and in response to this, the display interface module 36 displays the combined image in which the navel is in a desired direction (For example, up.) on the display 31.

Figure 18:
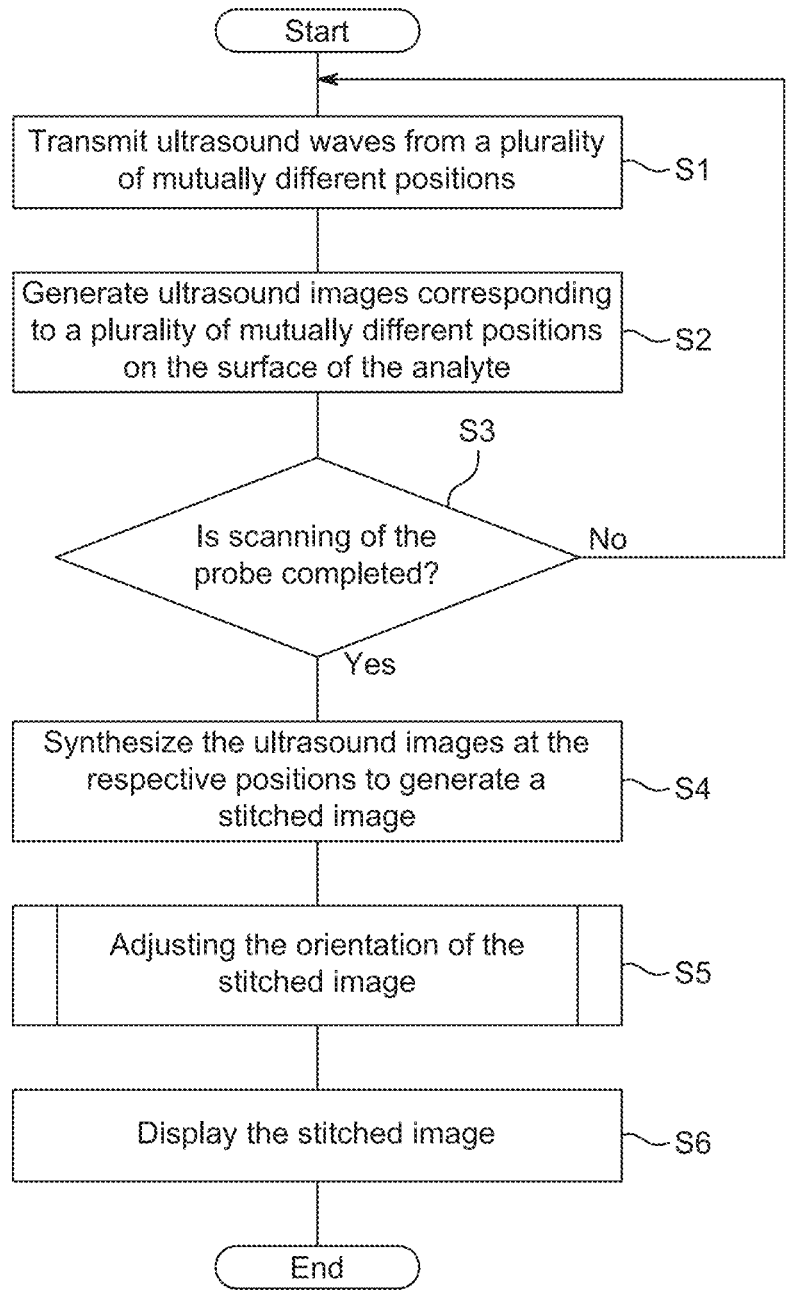
FIG. 18 is a flowchart showing the processing procedure of the ultrasound imaging method according to the second embodiment.

FIG. 18 is a flowchart showing a processing procedure of the ultrasound imaging method according to the present embodiment. In the flowchart shown in FIG. 18, the overall processing procedure is the same as that of the flowchart shown in FIG. 11, but step S5 for adjusting the orientation of the stitched image is replaced by step S5'.

Figure 19:
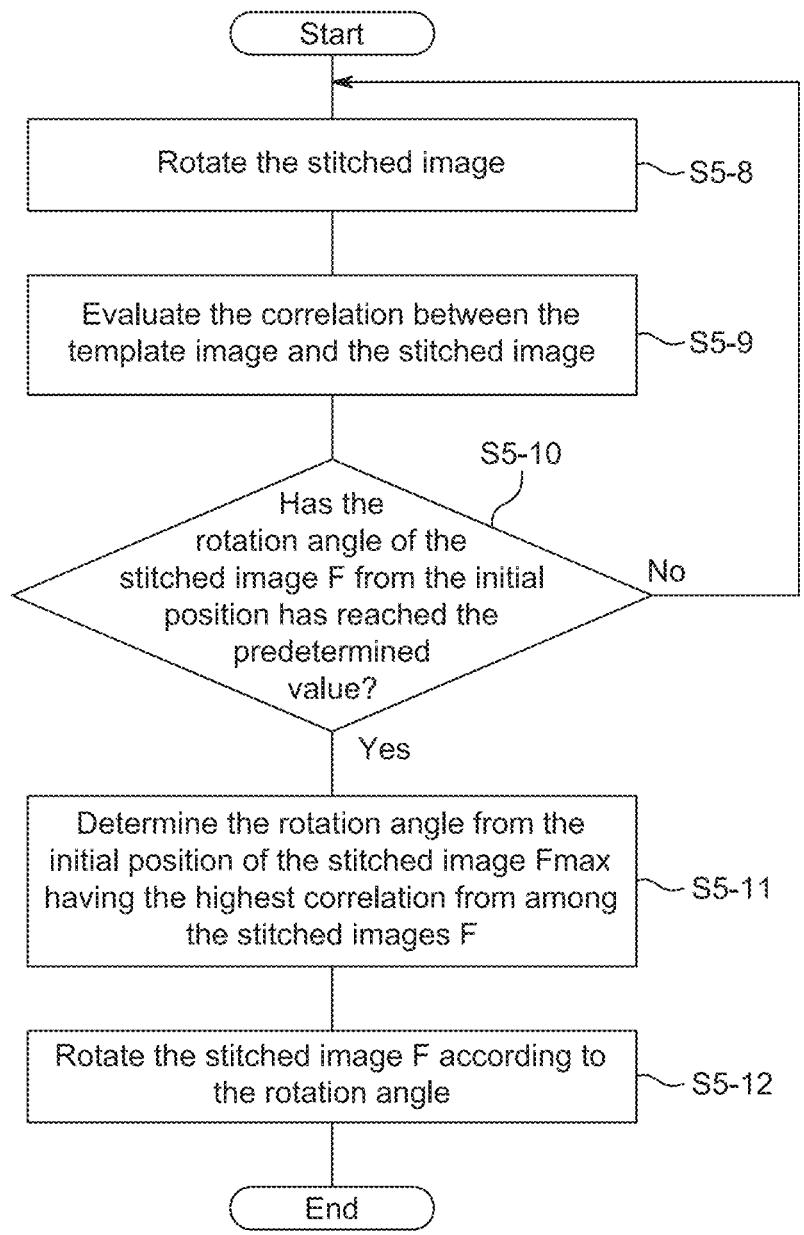
FIG. 19 is a flowchart showing a detailed processing procedure of the direction adjusting step in the second embodiment.

FIG. 19 is a flowchart showing the detailed processing procedure of step S5' in this embodiment. Step S5' includes steps S5-8 through S5-12.

First, in step S5-8, the virtual rotation module 14 e shown in FIG. 353 rotates the stitched image F, for example, by 1°.

In step S5-9, the correlation evaluation module 353f evaluates the correlation between the template image T and the stitched image F while virtually moving the rotated stitched image F.

In step S5-10, it is checked if the rotation angle of the stitched image F from the initial position has reached the predetermined value. If the rotation angle does not reach the predetermined value (For example, 45°), the process returns to step S5-8. Steps S5-8 and S5-9 are repeated until the rotation angle from the initial position of the stitched image F reaches a predetermined value.

Then, in step S5-11, the angle determination module 353g determines, as the rotation angle of the stitched image F, the rotation angle from the initial position of the stitched image Fmax having the highest correlation from among the stitched images F having the evaluated correlation.

Subsequently, in step S5-12, the rotation module 353*h* rotates the stitched image F according to the rotation angle determined by the angle determination module 353*g*.

As described above, in this embodiment, the orientation of the stitched image is adjusted by comparing the stitched image with the template image while rotating the stitched image. Unlike the first embodiment which utilizes the left-right symmetry of the biological tissue, the present embodiment can adjust the orientation of a stitched image of any portion which does not include the left-right symmetric tissue.

The present invention is not limited to the above embodiments, and various modifications can be made within the scope of the claims, and forms obtained by appropriately combining the technical means disclosed in each embodiment are also within the scope of the present invention.

In the above embodiment, the orientation of the stitched image of the abdominal section is adjusted so that the navel portion faces upward, but the orientation of the stitched image can be appropriately changed. For example, the orientation of the stitched image may be adjusted so that the navel portion is in the downward or lateral direction.

Further, in the above embodiment, the orientation of the stitched image is adjusted by utilizing the left-right symmetry of the biological tissue or by comparing the stitched image with the template image, but the method for adjusting the orientation of the stitched image is not limited thereto. For example, in the case of a stitched image of an abdominal section, the height of the right end portion of the left side corresponding to the contact positions of the probe 2 at the start and the end of scanning may be made equal, or the height of the navel portion may be adjusted so as to be upward.

Further, in the above embodiment, in order to obtain ultrasound images corresponding to a plurality of different positions on the surface of the analyte 9, ultrasound waves are intermittently transmitted from the probe 2 while the probe 2 is moved along the surface of the analyte 9. For example, a plurality of ultrasound transmitter-receivers may be arranged in the analyte 9, and ultrasound waves may be transmitted simultaneously from each ultrasound transmitter-receiver.

While the present invention is applicable to both medical and non-medical applications, it is particularly suitable for applications in which an analyte who is not a medical practitioner routinely confirms his or her health.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms) Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor module (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface." The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated" and other such relational terms should be construed, unless otherwise noted, to include removable, moveable, fixed, adjustable, and/or releasable connections or attachments. The connections/attachments can include direct connections and/or connections having intermediate structure between the two components discussed.

Numbers preceded by a term such as "approximately," "about," and "substantially" as used herein include the recited numbers, and also represent an amount close to the stated amount that still performs a desired function or achieves a desired result. For example, the terms "approximately," "about," and "substantially" may refer to an amount that is within less than 10% of the stated amount. Features of embodiments disclosed herein preceded by a term such as "approximately," "about," and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. An ultrasound imaging apparatus comprising:
    processing circuitry configured
        to receive a plurality of ultrasound waves transmitted from a plurality of mutually different positions on a surface of an analyte toward an interior of the analyte and reflected therein;
        to generate a plurality of ultrasound images corresponding to the respective positions, respectively;
        to stitch the plurality of ultrasound images at the respective positions to generate a stitched image of the cross section of the analyte; and
        to adjust an angle of the stitched image and directing a specific portion included in the stitched image in a predetermined direction.

2. The ultrasound imaging apparatus according to claim 1, wherein
    the specific portion includes a navel portion of an abdomen; and
    the processing circuitry aligns the navel portion with a desired direction of the image display when the stitched image is displayed on a screen.

3. The ultrasound imaging apparatus according to claim 1, wherein
    the processing circuitry is further configured
        to set one or a plurality of regions having a shape of line symmetry with respect to a central axis at an arbitrary position and an arbitrary angle in the stitched image;
        to evaluate symmetry of each of left and right images in the region with respect to the central axis;
        to select a region on the basis of the symmetry; and
        to calculate an angle difference between a predetermined axis passing through the stitched image and the central axis of the selected region.

4. The ultrasound imaging apparatus according to claim 3, wherein
    the processing circuitry sets the region by aligning the central axis of the region with an axis indicating a transmission direction of an ultrasound wave at a position on the surface of the analyte.

5. The ultrasound imaging apparatus according to claim 3, wherein
    the processing circuitry sets the respective regions by aligning central axes of the respective regions with respective axes indicating the transmission directions of the ultrasound waves at the plurality of different positions.

6. The ultrasound imaging apparatus according to claim 3, wherein
    the processing circuitry
        sets the region to be movable to the stitched image; and
        evaluates symmetry every time the region is moved.

7. The ultrasound imaging apparatus according to claim 6, wherein
    the processing circuitry selects a region having symmetry equal to or greater than a predetermined threshold among respective symmetry.

8. The ultrasound imaging apparatus according to claim 6, wherein
    the processing circuitry selects a region having highest symmetry among the regions.

9. The ultrasound imaging apparatus according to claim 3, wherein
the processing circuitry selects a central ultrasound image corresponding to a substantially central portion in the order of generation among the plurality of ultrasound images.

10. The ultrasound imaging apparatus according to claim 3, wherein
the processing circuitry
sequentially selects, from among the plurality of ultrasound images, the central axis of the central ultrasound image corresponding to the substantially central portion in the order of generation and the central axis of a predetermined number of ultrasound images in the order of generation before and after the central ultrasound image, and
sets the region by aligning the central axis of the central ultrasound image with the selected central axis.

11. The ultrasound imaging apparatus according to claim 1, wherein
the processing circuitry is further configured
to virtually rotate at least one of a template image of an ultrasound stitched image and the stitched image, the template image including the specific portion and in which the specific portion is oriented in the predetermined direction;
to evaluate the correlation between the template image and the stitched image;
to determine a rotation angle of the stitched image based on the correlation;
to rotate the stitched image according to the rotation angle.

12. The ultrasound imaging apparatus according to claim 11, wherein
the processing circuitry evaluates the correlation between the template image and the stitched image each time the stitched image is rotated.

13. The ultrasound imaging apparatus according to claim 11, wherein
the processing circuitry determines, as the rotation angle, an angle with respect to an initial position of the stitched image having the highest correlation among the stitched images.

14. The ultrasound imaging apparatus according to claim 2, wherein
the processing circuitry is further configured
to set one or a plurality of regions having a shape of line symmetry with respect to a central axis at an arbitrary position and an arbitrary angle in the stitched image;
to evaluate symmetry of each of left and right images in the region with respect to the central axis;
to select a region on the basis of the symmetry; and
to calculate an angle difference between a predetermined axis passing through the stitched image and the central axis of the selected region.

15. The ultrasound imaging apparatus according to claim 14, wherein
the processing circuitry sets the region by aligning the central axis of the region with an axis indicating a transmission direction of an ultrasound wave at a position on the surface of the analyte.

16. The ultrasound imaging apparatus according to claim 14, wherein
the processing circuitry sets the respective regions by aligning central axes of the respective regions with respective axes indicating the transmission directions of the ultrasound waves at the plurality of different positions.

17. The ultrasound imaging apparatus according to claim 4, wherein
the processing circuitry
sets the region to be movable to the stitched image; and
evaluates symmetry every time the region is moved.

18. The ultrasound imaging apparatus according to claim 5, wherein
the processing circuitry
sets the region to be movable to the stitched image; and
evaluates symmetry every time the region is moved.

19. An ultrasound imaging method, comprising:
receiving a plurality of ultrasound waves transmitted from a plurality of mutually different positions on the surface of the analyte toward the interior of the analyte and reflected therein;
generating a plurality of ultrasound images corresponding to the respective positions, respectively;
stitching the plurality of ultrasound images at respective positions to generate a stitched image of the cross section of the analyte; and
adjusting an angle of the stitched image and directing a specific portion included in the stitched image in a predetermined direction.

20. A non-transitory computer-readable recording medium storing a program causing a processor of an ultrasound imaging apparatus to execute processing, the processor configured to control operation of the ultrasound imaging apparatus, the processing comprising:
receiving a plurality of ultrasound waves transmitted from a plurality of mutually different positions on the surface of the analyte toward the interior of the analyte and reflected therein;
generating the plurality of ultrasound images corresponding to the respective positions, respectively;
stitching the plurality of ultrasound images at the respective positions to generate a stitched image of the cross section of the analyte; and
adjusting an angle of the stitched image and directing a specific portion included in the stitched image in a predetermined direction.

* * * * *